United States Patent
Dominick et al.

(10) Patent No.: US 10,599,812 B2
(45) Date of Patent: Mar. 24, 2020

(54) PREPROCESSING IMAGE DATA BASED ON SCAN PROTOCOLS

(71) Applicants: Lutz Dominick, Eggolsheim (DE); Vladyslav Ukis, Nürnberg (DE)

(72) Inventors: Lutz Dominick, Eggolsheim (DE); Vladyslav Ukis, Nürnberg (DE)

(73) Assignee: Siemens Healthcare GmbH, Erlangen (DE)

(*) Notice: Subject to any disclaimer, the term of this patent is extended or adjusted under 35 U.S.C. 154(b) by 606 days.

(21) Appl. No.: 15/223,439

(22) Filed: Jul. 29, 2016

(65) Prior Publication Data

US 2018/0032556 A1 Feb. 1, 2018

(51) Int. Cl.
*G06F 19/00* (2018.01)
*G16H 30/20* (2018.01)
*G16H 30/40* (2018.01)

(52) U.S. Cl.
CPC ........... *G06F 19/321* (2013.01); *G16H 30/20* (2018.01); *G16H 30/40* (2018.01)

(58) Field of Classification Search
CPC ...... G06F 19/321; G06F 19/00; G06F 16/217; G06F 19/328; G16H 30/20; G16H 50/70; G16H 30/40; G06K 2209/05; G06K 9/4676; G06K 9/6212; G06T 11/60; G06T 2207/10081; G06T 2207/10084; G06T 2207/10088; G06T 2207/10104; G06T 2207/10108; G06T 2207/30096; G06T 7/0012; A61B 5/0013; A61B 6/0414; A61B 6/463; A61B 6/465; A61B 6/469; A61B 6/502; A61B 6/5241; A61B 6/563; G06N 5/02; G06N 5/022; G06Q 10/00; Y10S 378/901
USPC ........................................................ 707/751
See application file for complete search history.

(56) References Cited

U.S. PATENT DOCUMENTS

| | | | |
|---|---|---|---|
| 6,891,920 B1* | 5/2005 | Minyard | A61B 6/469 378/37 |
| 2003/0013951 A1* | 1/2003 | Stefanescu | G06F 19/321 600/407 |
| 2006/0109500 A1* | 5/2006 | Morita | G06F 3/1208 358/1.15 |
| 2007/0109294 A1* | 5/2007 | Gotman | A61B 6/00 345/418 |
| 2007/0127795 A1* | 6/2007 | Lau | G06F 17/3028 382/128 |
| 2007/0237380 A1* | 10/2007 | Iwase | A61B 6/032 382/131 |
| 2008/0119717 A1* | 5/2008 | Profio | G06F 19/321 600/407 |
| 2008/0123912 A1* | 5/2008 | Lal | G06T 5/002 382/128 |
| 2010/0008475 A1* | 1/2010 | Maschke | A61B 5/06 378/209 |

(Continued)

*Primary Examiner* — Evan Aspinwall
(74) *Attorney, Agent, or Firm* — Lempia Summerfield Katz LLC (57) ABSTRACT

A system and method for optimizing preprocessing of medical images. Preprocessing is triggered by receiving scan results and a scan protocol without input from a reading room or user interface. The preprocessing tasks are optimized through use of matching scan protocols to sets of possible preprocessing tasks. The execution of the preprocessing tasks is optimized through use of feedback from the reading room.

18 Claims, 4 Drawing Sheets

(56) References Cited

U.S. PATENT DOCUMENTS

| | | | | |
|---|---|---|---|---|
| 2010/0040268 A1* | 2/2010 | Boeing | .......... | A61B 6/482 |
| | | | | 382/128 |
| 2010/0260399 A1* | 10/2010 | Hajnal | .......... | G06F 19/321 |
| | | | | 382/131 |
| 2013/0090946 A1* | 4/2013 | Foo | .......... | G06Q 10/06 |
| | | | | 705/3 |
| 2013/0311472 A1* | 11/2013 | Cohen-Solal | .......... | G06F 19/321 |
| | | | | 707/737 |
| 2014/0088984 A1* | 3/2014 | Oh | .......... | G01R 33/543 |
| | | | | 705/2 |
| 2014/0348401 A1* | 11/2014 | Xu | .......... | A61B 6/545 |
| | | | | 382/128 |
| 2015/0085971 A1* | 3/2015 | Braun | .......... | A61B 6/032 |
| | | | | 378/8 |
| 2015/0100572 A1* | 4/2015 | Kalafut | .......... | G06Q 50/24 |
| | | | | 707/736 |
| 2015/0182173 A1* | 7/2015 | Yang | .......... | A61B 5/7289 |
| | | | | 600/407 |

* cited by examiner

PREPROCESSING IMAGE DATA BASED ON SCAN PROTOCOLS

TECHNICAL FIELD

The present embodiments relate to preprocessing image data from medical imaging devices.

BACKGROUND

Medical diagnostic applications for reading and reporting may be used to evaluate medical images from medical imaging devices. A scan is conducted by an imaging device. The scan data is then stored until requested by a user. Once requested, the scan data is displayed to the user. Once requested, the scan data may require extensive processing in order to be usable or displayed by the medical diagnostic application. Large outlays of resources may be used to transform the scan data into a visual representation.

Processing tasks may be directed by the display applications or initiated by a user at a workstation in a reading room. Processing tasks done in the reading room generate inefficiencies in resources and timing. In addition to any delays produced by starting processing later, the resource intensive activities involved in processing have to compete with other active processes initiated by the user, bogging down the workstations in the reading room.

BRIEF SUMMARY

Embodiments are provided for optimizing preprocessing scan data from a medical image device.

In one aspect, a system for preprocessing scan data is provided. A preprocessing database is configured to store a plurality of preprocessing tasks and usage data for usage of the preprocessing tasks. A preprocessing processor is configured to match a scan protocol related to the scan data to one or more of the preprocessing tasks of the plurality of preprocessing tasks. The preprocessing processor is further configured to execute the one or more preprocessing tasks on the scan data based on the match. A workstation is configured to receive the preprocessed scan data. The workstation is further configured to transmit usage data to the preprocessing database.

In a second aspect, a method is provided for preprocessing scan data. Scan data is received scan data including scan protocol data for a scan by a medical imaging device. A preprocessing database is queried for a plurality of preprocessing tasks related to the scan protocol data. A ranking of the plurality of preprocessing tasks is identified based on usage data related to the scan protocol data and the plurality of preprocessing tasks. The plurality of preprocessing tasks are performed on the scan data in the ranked order.

In a third aspect, an apparatus for preprocessing scan data. Scan data is received from a scan including image data and a scan protocol. The scan data protocol is matched to one or more preprocessing tasks. A score is calculated for each of the preprocessing tasks. The image data is processed using the scored preprocessing tasks, the higher scored preprocessing tasks are processed first. The processed image data is transmitted to a workstation.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale; emphasis instead being placed upon illustrating the principles of the invention. Moreover, in the figures, like reference numerals designate corresponding parts throughout the different views.

DETAILED DESCRIPTION

Image processing of medical images may require vast amounts of computing resources. Segmentation, rendering, modeling, detection, or other image processing using acquired scan data is processing intensive. Advanced imaging processing techniques are used to generate increasingly complex medical images ranging from two-dimensional images to fully developed anatomical models. The techniques create an ever increasing burden for even the most advanced image processing centers. Processing of medical images may thus take from minutes to hours. A user who is trying to evaluate a set of medical image data may have to wait for an extended period of time while a display application in a reading room prepares the image data for viewing. The processed images are sometimes not even used or evaluated.

Certain processing tasks may be done ahead of time in the reading room. Processing at the reading room still delays the evaluation of the image data. Without guidance, many of the preprocessing tasks may go to waste. A user may order the wrong kind or type of imaging during an appointment and end up with multiple scans from various devices. Each scan may then be preprocessed even though many of the scans will never be used. Inefficient processing leads to wasted time and resources.

The disclosed embodiments provide systems and methods for optimizing preprocessing of medical images. Preprocessing is triggered by receiving scan results and a scan protocol without input from a reading room or user interface. The preprocessing tasks are optimized through use of matching scan protocols to sets of possible preprocessing tasks. The execution of the preprocessing tasks is optimized through use of feedback from the reading room.

Embodiments may be implemented to exclude certain image processing tasks leading to an improvement in an image processing system. Certain computational tasks are prioritized to improve the efficiency and function of the image processing system. The increased efficiency and usage of resources may lead to quicker turnaround times, faster evaluation of medical images, smaller memory requirements, and/or less dead time for users.

Scan data relating to a scan is received from a medical imaging device. The scan data may include image data and data that identifies parameters and/or a protocol of the scan. Potential preprocessing tasks are identified. The preprocessing tasks are ranked and then executed in the ranked order. The preprocessed data is then transmitted to a user interface.

Figure 1:
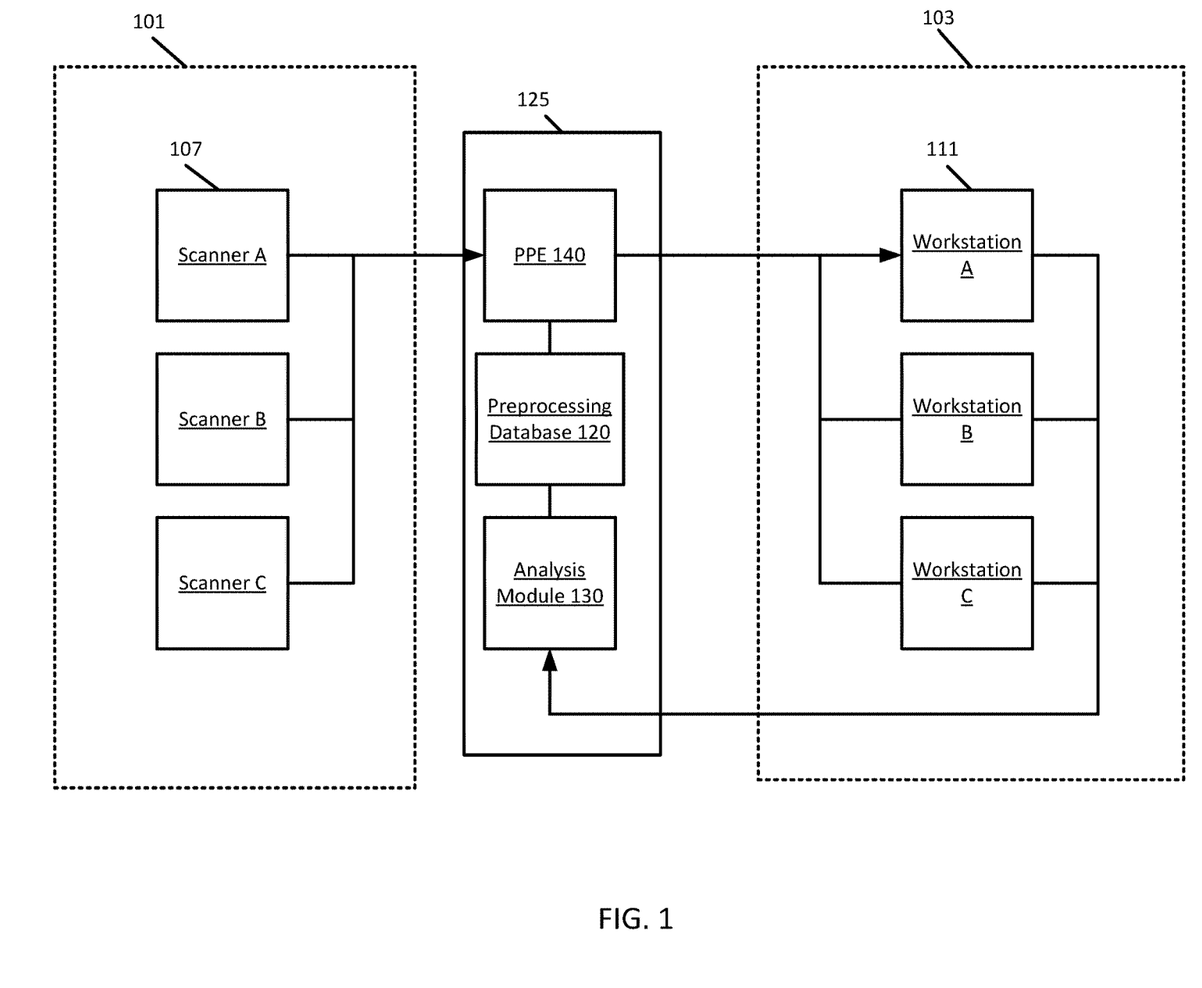
FIG. 1 depicts an example system for preprocessing image data based on scan protocols.

FIG. 1 illustrates an example system for preprocessing image data based on scan protocols. The system includes a plurality of medical imaging devices 107 also referred to as scanners or scanning devices or imaging devices. The medical imaging devices 107 are configured to generate image data that is transmitted to the preprocessing engine 140 (PPE) and to one or more workstations 111 for evaluation. The PPE 140 may be configured to determine preprocessing tasks to be run on the image data. The PPE 140 may select one or more preprocessing tasks from a preprocessing database 120 based on information from an analysis module 130. The PPE 140, the preprocessing database 120 and the analysis module 130 may be part of a preprocessing server 125. Additional, different or fewer components may be included. For example, the system may include only one scanner 107 or one workstation 111. The system may include additional medical imaging components such as a picture archiving and communication system (PACS). A PACS may store the image data and preprocessed image data prior to be transmitted to the user workstation 111. The system may also include additional networking or storage devices configured assist the transmission of data from a medical imaging device 107 to a workstation 111.

The system in FIG. 1 includes two zones where some of the components reside. The hospital scanner center 101 may include the medical imaging devices 107. The reading room 103 may include the one or more reading workstations 111. The PPE 140, the analysis module 130, and the preprocessing database 120 may reside either in the hospital scanner center 101 or elsewhere on a hospital's network, or at a remote location. The PPE 140, the analysis module 130 and the preprocessing database 120 may also reside in the cloud. The PPE 140, the analysis module 130, and the preprocessing database 120, however, are located separately from the reading workstations 111.

The system in FIG. 1 includes one or more medical imaging devices 107. The medical imaging devices 107 are different modalities, such as an ultrasound scanner, a CT scanner, and an MRI scanner. In other embodiments, two or more of the medical imaging devices are of a same modality, such as two x-ray scanners. The medical imaging devices 107 may also be referred to as medical scanning devices, imaging devices or scanning devices. The one or more medical imaging devices 107 may include imaging devices such as magnetic resonance image (MRI) scanners, positron emission tomography (PET) scanners, Single-photon emission computed tomography (SPECT) scanners, ultrasound devices, tomography devices, among others. The medical imaging devices 107 may include any type of imaging device or medical diagnostic device that is connected to a medical or hospital network. Each medical imaging device 107 may be configured to generate data (such as image data) relating to an object (e.g. a patient or a portion of the patient). The medical imaging devices 107 may operate using a formatting standard such as the DICOM standard. DICOM is a standard used for storage and transmission of medical image data including for example, 2D, 3D, and video images. The medical imaging devices 107 may operate using alternative standards such as the Health Level-7 (HL7) standard. Other formats or standards may be used by different devices.

The scan data from the medical imaging device 107 may include both scan results and administrative data related to the scan or study. The scan results may include image data or other diagnostic data. Image data is data representing the patient that may be used to generate an image of the patient. The data is formatted for display (e.g., RGB values) or as scalars based on the scanning. Any format may be used for the image data. The medical imaging device 107 may generate one or more two-dimensional images that are subsequently stitched together to create a three-dimensional image or a moving image. The administrative data may include information regarding the scan protocol (e.g. the type of scan, the region of the body, patient information). For example, when using the DICOM standard, the administrative data may include a network message that is initiated by the scanning equipment. The message, referred to as a modality performed procedure step (MPPS), is also sent to the PACS and/or other systems such as a radiology information system (RIS). The message carries information about the settings for the scan that was performed by the medical imaging device 107 during acquisition. The MPPS may be a trigger (along with the scan results) for starting preprocessing. Once the MPPS and scan results have been received, the preprocessing tasks may begin without further input.

In certain embodiments, the scan data may include additional scan protocol data. The scan data may contain a unique identifier for the scan or the study. The scan data may contain data related to the type of equipment that originally acquired the scan data. The scan data may include data related to the manufacturer, data related to the manufacturer's model name, a description of the study or series of images, an identifier for the acquisition protocol, the target region, the acquisition type, the procedure context, the acquisition parameters (e.g. exposure time, scanning length), the dose etc.

In certain embodiments, the scan data includes data related to a predetermined scan protocol. For example, the medical imaging device 107 may have one or more stored workflows for commonly run scanning protocols. The scan data is for this predetermined scan protocol, so may also be predetermined. In certain embodiments, the scan data may include any adjustments made to the parameters by a user.

The scan data may be stored in a PACS. A PACS is a computing system used to transfer, store, display, and manage medical images and associated administrative data. The PACS may store raw unprocessed data, preprocessed data, or fully processed data. The PACS may use the DICOM standard for storage. The PACS may receive requests from the reading workstation 111 for images or studies. The PACS may preprocess or process the image data stored within.

The trigger for beginning preprocessing may be receiving the scan data including the MPPS message (or equivalent transactional message). In certain embodiment, the completion of a scan or study is a trigger to begin preprocessing. A scan or study may generate data over a period of time. Data generated at the beginning may begin preprocessing as soon as possible to cut down on wait time. In certain embodiments, preprocessing of the image data may begin as soon as a scan has completed or during the scan.

Referring back to FIG. 1, the reading workstation 111 (also referred to as a workstation or user interface 111) may include one or more workstations or computing devices. The reading workstation 111 may be at the acquisition workplace or in a separate area such as a reading room. The reading workstation 111 may be remote from the site or hospital and connected to the hospital network though, for example, a virtual private network or other secure connection. The reading workstation 111 may include processing capabilities configured to process the images for display. The images or the preprocessed images may be processed or further processed at the reading workstation 111. In certain embodiments, any processing done at the reading workstation 111 may be recorded along with the type of images processed. The processing tasks may be sent as feedback to the analysis module 130 or the PPE 140. The workstations 111 may be configured to display or present the image data to a technician or end user.

In certain embodiments, the reading workstation 111 may record user preferences for each application used. The reading workstation 111 may, for example, record which preprocessed images are viewed first and which preprocessed images are not viewed at all. The reading workstation 111 may record each user's actions and preferences for each type of scan and each type of preprocessed image data.

The preprocessing server 125 may include the PPE 140, the preprocessing database 120 and the analysis module 130. The preprocessing server 125 may receive scan data including the scan protocol (e.g. MPPS) and scan results. The preprocessing server 125 may output preprocessed data to the workstation 111. The preprocessing server may receive input from the workstations 111 regarding the usage of the preprocessed data.

The PPE 140 may be configured to match the scan protocol data and other scan information (modality, body region(s), e.g.) to an initial set of best practices or common preprocessing tasks or workflows. The PPE 140 may be configured to search a preprocessing database 120 that contains types of scans and related preprocessing tasks. For example, the database 120 may contain a data entry for scan protocol A and scan protocol B. The database 120 may also contain a data entry for preprocessing tasks W, X, Y, and Z. The entry for scan protocol A may identify preprocessing tasks W, X, and Y as best practice preprocessing tasks for scan protocol A. The entry for scan protocol B may identify preprocessing tasks W, Y, and Z as best practice preprocessing tasks for scan protocol B. Alternatively, or in addition to being associated with a scan protocol, the tasks or workflows in the database 120 may be sorted by modality, type of scanner, or body region. Certain tasks may be used by certain types of scanners or primarily used only for certain objects or body regions.

In certain embodiments, the PPE 140 processes the image data using the matched preprocessing tasks. The resulting processed data is transmitted to the user workstation 111. The original data may be transmitted to the user workstation 111 from the imaging device 107 or the PACS. The preprocessed data may be transmitted to the PACS for storage or for later use. In certain embodiments, the PPE 140 identifies the preprocessing tasks and transmits the tasks to a different server or servers configured for processing image data. In certain embodiments, the PACS preprocesses the image data.

In certain embodiments, the preprocessing database 120 may contain a set of all preprocessing tasks for a given scan protocol. The set may include every possible preprocessing task or every preprocessing task that has previously been used for the given scan protocol. The set may be updated as additional tasks are used for the scan protocol. The set of preprocessing tasks may be configured using information from a vendor or user interface applications package. For example, when a device or interface is first used, the vendor may specify preprocessing tasks. The set of preprocessing tasks may be supplemented or altered over time. New tasks may be added based on usage data or new technology. Tasks may be removed that are never used or that have become obsolete.

The scan protocol or modality may be the primary search key when matching processing tasks. Anatomic details such as body region may be used as a secondary search criterion. Other scan data from the medical imaging device 107 may be used as search criterion. In certain embodiments, the preprocessing database 120 may return multiple results that are similar to the search criterion. For example, if there is an exact match, the preprocessing database 120 may return the exact match. However, if there is not an exact match, the preprocessing database 120 may return relevant results.

The preprocessing database 120 may contain a plurality of preprocessing task workflows that each contains one or more related tasks. The preprocessing database 120 may rank or score each workflow or task based on a score or preferences. For example, the workflows or tasks may be scored and ranked according to likelihood of being used. The workflows or tasks may be ranked according to which workflow or task results in processed image data that will be used first. For example, for a particular type of scan, a certain processed image is often viewed first by a user. The task that results in that processed image may be ranked higher than a task that generates a processed image that may be viewed less and/or at a later point in time. In certain embodiments, the preprocessing tasks may be performed in parallel.

The analysis module 130 may be configured to receive feedback from the reading workstation 111 regarding the scan protocols, modality, and the usage of the processed images. The analysis module 130 may optimize the priority of the possible preprocessing tasks for each scan protocol. The analysis module 130 identifies processed data has been created interactively by the user and assigns the related task to the set of tasks related to the scan protocol for subsequent preprocessing activities. In certain embodiments, the analysis module 130 may identify a new task requested or performed by a user. In other embodiments, the analysis module 130 may receive information regarding existing tasks in the database 120.

The analysis module 130 may receive feedback regarding which tasks are the most useful. The feedback may include the order of images evaluated, the time subsequent to the scan that the images are evaluated, the types of further imaging processing done on the images, and/or the relative value of each of the processed images (e.g. how useful to the user was the image measured by dwell or view time) among others. The feedback may be sorted based on the individual scan protocols, the type of scan, the imaging device used, the type of imaging device used, the region of the body scanned, the patient, and/or specific user preferences. For example, an image A is generated by an imaging device B depicting the body region C using a scan protocol D. The image A is preprocessed using a workflow 01 stored in memory that corresponds to imaging device B, body region C and scan protocol D. A user evaluated the processed image and chooses to further process the image using a workflow 02. The user further decides to process the image using a workflow 03. The user makes an evaluation using the image processed using workflow 03. The entire process is recorded and transmitted to the analysis module 130. The analysis module 130 may determine that workflow 01 is not as useful as workflow 03 and as such workflow 01 is downgraded or ranked lower in the database 120. Workflow 02, similarly was not useful, but still requested by the user. For a second image generated at a later time using data from the imaging device B depicting the body region C using the scan protocol D, the database 120 may list workflow 03 as being the top priority followed by workflow 01 and workflow 02. The change in rankings may or may not occur following a single use, but rather may be changed after a number of instances or using statistical information (e.g., relative rates of usage).

In certain embodiments, each preprocessing task or workflow may be scored and/or ranked. The score may be indicative of how useful or efficient the preprocessing task is. For example, a preprocessing task A may lead to a useful processed image 75% of the time for a specific scan protocol. Preprocessing task B may lead to a useful processed image 70% of the time for the specific scan protocol. Preprocessing task A may then be ranked higher than preprocessing task B and subsequently be executed first and potentially more often. In certain embodiments, there may be a cutoff of the score for each scan protocol. Scan protocol A may only run preprocessing tasks that have a useful score above 50% while scan protocol B may run only tasks that have a useful score above 80%. In certain embodiments, the preprocessing tasks may be scored as a function of the scan protocol, modality, user, body region, among other criteria. The scores may be a function of the efficiency of the preprocessing task (how often the preprocessing task leads to a useful result), the resources consumed (there may be less risk for preprocessing tasks that do not use many resources), user ratings (may be collected at the beginning or end of the evaluation), vendor input (suggested preprocessing tasks by the vendor may be scored higher), among others. The preprocessing tasks may be scored individually or grouped as a workflow. The scores for the preprocessing tasks may change over time as usage data is collected for each preprocessing task.

In certain embodiments, the analysis module 130 may discount outlier uses or weigh certain uses differently when scoring or ranking the preprocessing tasks. For example, the analysis module 130 may exclude certain uses if the uses do not appear to follow a pattern. For example, a new user may view every single possible image at first while learning how to evaluate images. Such uses may not be helpful in determining a set of best practices for preprocessing. In another example, if the uses for a user are drastically different from the uses of the rest of the users, those uses may be weighted less or excluded.

In certain embodiments, the analysis module 130 may use machine learning to recognize patterns in the usage of the images. The patterns may be used to predict the best practices for preprocessing. The analysis module 130 may be given a set of scan protocols and the related uses and determine possible clusters or patterns. Machine learning may identify preprocessing tasks that may be helpful across different modalities or scan protocols.

In certain embodiments, the analysis module 130 may share data with other analysis modules from other site or hospitals. The shared data may include the scan data such as the scan protocol, the usage data, the associated best practice preprocessing tasks and the scores or ranks. With a larger set of data, the analysis module 130 may be capable of generating better predictions and as a result, offer better preprocessing.

The analysis module 130 may generate the preprocessing workflows for the scan protocols in the database 120. The initial workflows may be generated by a vendor of an imaging device or user interface software. The initial workflows may be empty or generated by a user or administrator. As the analysis module 130 receives feedback regarding each workflow, the analysis module 130 may change the workflow. In certain embodiments, the analysis module 130 may assign an initial set of preprocessing tasks to a brand-new scan protocol based on data such as modality and body region in the scan protocol. Subsequent feedback may optimize the initial set later on.

Figure 2:
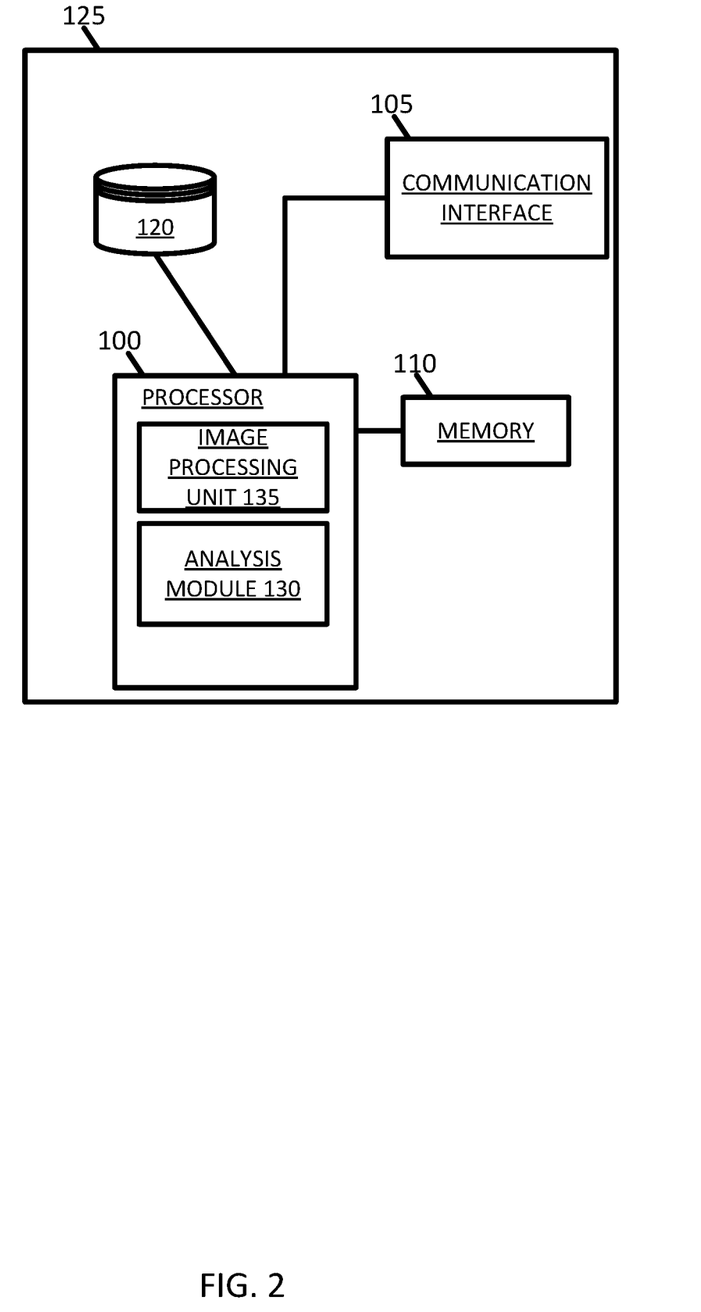
FIG. 2 depicts an example preprocessing server.

FIG. 2 illustrates an example preprocessing server 125. The preprocessing server 125 may be configured to receive scan data. The preprocessing server 125 may be configured to select one or more preprocessing tasks and process the scan data using the one or more preprocessing tasks. The preprocessing server 125 includes a processer 100, a memory 110, a preprocessing database 120, and a communications interface 105. The processor 100 may include an image processing unit 135 and an analysis module 130.

The processor 100 may include a general processor, digital signal processor, an application specific integrated circuit (ASIC), field programmable gate array (FPGA), analog circuit, digital circuit, combinations thereof, or other now known or later developed processor. The processor 100 may be a single device or combinations of devices, such as associated with a network, distributed processing, or cloud computing.

The memory 110 may be a volatile memory or a non-volatile memory. The memory 110 may include one or more of a read only memory (ROM), random access memory (RAM), a flash memory, an electronic erasable program read only memory (EEPROM), or other type of memory.

The communication interface 105 may include any operable connection. An operable connection may be one in which signals, physical communications, and/or logical communications may be sent and/or received. An operable connection may include a physical interface, an electrical interface, and/or a data interface. The communication interface 105 provides for wireless and/or wired communications in any now known or later developed format. In one embodiment, the communication interface 105 is a network interface card or cards.

The preprocessing database 120 may be a database, data store, or data structure configured to store data entries for preprocessing tasks and scan protocols. The preprocessing database 120 may store usage data relating to the preprocessing tasks and the scan protocols. The preprocessing database 120 may store scores or rankings relating to the preprocessing tasks and scan protocols. The preprocessing tasks and/or scan protocols are stored in the memory 110, the preprocessing database 120, or other locations.

The image processing unit 135 may be configured to process image data. The image processing unit 135 may use one or more selected preprocessing tasks to process received image data from a medical imaging device 107. The image processing unit 135 may include one or more processors (such as graphics processors) and one or more memories that are configured to implement the one or more selected preprocessing tasks.

The analysis module 130 may be configured to analyze usage data received from a reading workstation 111 or user interface 111. The analysis module 130 may be configured to score or rank preprocessing tasks based on the usage data or other criteria. The analysis module 130 may be configured to use machine learning to determine best practice preprocessing tasks for one or more scan protocols.

Figure 3:
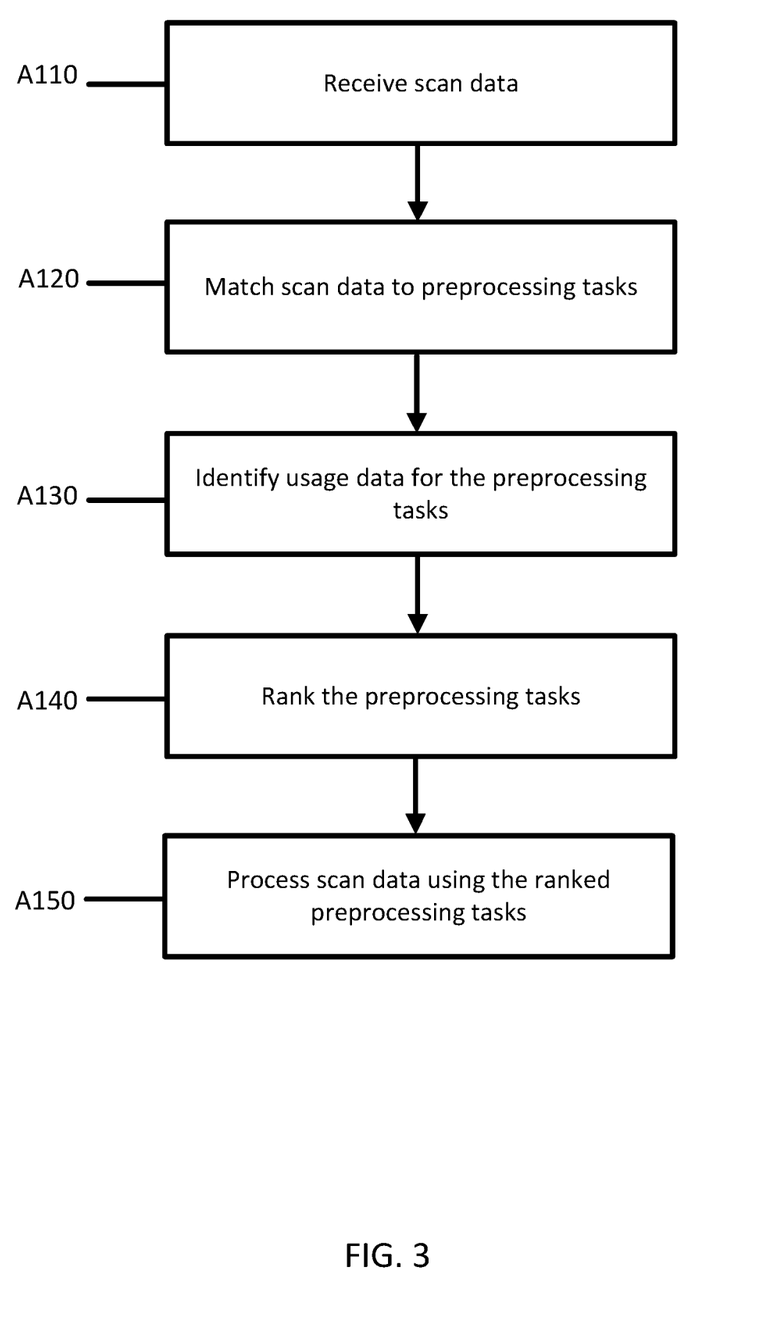
FIG. 3 depicts an example method for preprocessing image data based on scan protocols using the preprocessing server of FIG. 2.

FIG. 3 depicts an example method for preprocessing image data based on scan protocols using the preprocessing server 125 of FIG. 2. In one embodiment, the acts are performed by the preprocessing server 125, the PPE 140, or one or more of the imaging devices 107. Additional, different, or fewer acts may be provided. For example, acts A130 and A140 are not performed, but instead the results of previous performance of the acts are used in act A120. The acts are performed in the order shown or other orders. The acts may also be repeated. In certain embodiments, the method may begin immediately following completion of a scan. In certain embodiments, the method may begin as soon as a portion of image data of a larger study has been generated by the imaging devices 107.

At act A110, scan data including scan results and a scan protocol is received. The scan protocol may be a MPPS transaction message. The reception of the scan results and a MPPS message may be a trigger to begin preprocessing. No other input may be needed.

The scan data may be received from a medical imaging device 107 such as a magnetic resonance imaging (MRI) scanner, a positron emission tomography (PET) scanner, a single-photon emission computed tomography (SPECT) scanner, an ultrasound scanner, a tomography device, among others. The medical imaging device 107 may include any type of imaging device, medical diagnostic device, and/or therapy device that is connected to a medical or hospital network. The scan data may be received using the communications interface 105. The scan data may be stored in the memory 105. The scan data may be received from a Picture Archiving and Communication System (PACS). The scan data may be formatting using a standard formatting scheme such as DICOM or may be formatted in a proprietary format. Scan data may include metadata relating to or indicating the scan protocol. The metadata may contain one or more parameters or attributes that describe the scan.

In certain embodiments, the scan protocol may be explicitly identified such as through a unique scan protocol identifier in the scan data. For example, a finite number of scan protocols may be predefined by a user. The predefined scan protocols may be assigned an identifying serial number or reference number. In other embodiments, the scan protocol may be derived or identified from a header, metadata, accompanying order data, data entered by the user at the medical imaging device 107 or attributes of the scan data. The scan data may contain data related to the type of equipment that originally acquired the scan data. The scan data may include data related to the manufacturer. The scan data may include data related to the manufacturer's model name. The scan data may include a description of the study or series of images. The scan data may include further data such as an identifier for the acquisition protocol, the target region, the acquisition type, the procedure context, the acquisition parameters (e.g. exposure time, scanning length), the dose etc.

At act A120, the scan protocol is matched by the processor 100 to one or more preprocessing tasks. A preprocessing database 120 may store data entries for the one or more preprocessing tasks and data entries for the scan protocols. The one or more preprocessing tasks may include a super set of all preprocessing tasks that may be used for image data collected using the scan protocol. The preprocessing database 120 may store the relationships between the preprocessing tasks and the scan protocols, for example, which preprocessing tasks are commonly used for each of the scan protocols.

In certain embodiments, similar scan protocols may be grouped together. For example, two different scans that both involved similar modalities and similar body regions may be treated alike for the purposes of matching the scan protocol to preprocessing tasks. Minor differences in scan protocol may be ignored in order to generate a finite number of possible scan protocols to match against.

At act A130, usage data is identified by the analysis module 130 for the scan protocol. The usage data may include information relating to historical or past scans that included a similar scan protocol. The usage data may include information relating to preprocessing tasks for the past scans (that match the one or more preprocessing tasks from act A120) and whether or not preprocessing tasks led to a useful processed image. A prior similar scan, for example, may have used the preprocessing tasks A, B, and C. The resulting processed image was viewed and designated as useful by a user. A second prior similar scan, for example, may have used the preprocessing tasks A, D, and E and the resulting processed image was not viewed. A third prior similar scan, for example, may have used the preprocessing tasks B, C, F, and G. The resulting processed image was viewed and designated as useful by a user. Taken together, the three instances of usage data indicate that preprocessing tasks B, C, F, and G may be useful. Tasks D and E were not useful and task A was indeterminate. From this small sample size, B and C were 100% useful in getting an image that was useful. Task A was 50% successful. Tasks D and E were 0% successful.

At act A140, the one or more preprocessing tasks are ranked by the analysis module 130 using the usage data. Using the example given above for the usage data in act A130, the preprocessing tasks may be ranked based on their usefulness to the user. B, C, F, and G may be ranked highest. D and E may be ranked lowest. A ranking may thus be B, C, F, G, A, D, and then E. Tasks B and C may be ranked highest as the tasks were both used twice and had success rates of 100%. Tasks F and G were only used once, but had success rates of 100%. Task A was used twice and had a success rate of 50%. Tasks D and E had success rates of 0%.

In certain embodiments, the preprocessing tasks may be ranked according to success rate as shown above. Other criteria may be used instead or in addition to rank the preprocessing tasks. The time to preprocess the image data may be a factor in the rankings. For example, a task that takes a fraction of the resources of another task may be ranked higher. Even if the task is less successful in generated a useful image, the potential loss of resources may be less than that of a task that takes up a large amount of time and resources. The amount of time a user viewed an image generated by a preprocessing task may indicate priority.

In certain embodiments, a plurality of tasks may be grouped together to form a workflow. The workflow may be ranked instead of the individual preprocessing tasks.

At act A150, the scan data is processed by the image processing unit 135 in the order of the ranked preprocessing tasks. The most successful or most promising preprocessing tasks may be implemented first. In certain embodiments, the processed scan data is transmitted to a user interface 111 or PACS for storage.

In certain embodiments, there may be a cutoff or threshold for which preprocessing tasks are implemented and which preprocessing tasks are not. For example, only preprocessing tasks with a success rate above a predefined threshold may be executed. The predefined threshold may be set by an administrator or may reflect the amount of resources available for preprocessing. For example, if multiple scans are generated during a time period and the system only has resources to execute a certain number of preprocessing tasks in a time period, the system may set the threshold higher in order to limit the number of preprocessing tasks. Similarly, if there are free resources for preprocessing, the threshold may be lowered or eliminated. Alternatively, the threshold may be for a number of tasks and the tasks with the greatest ranking up to that number of tasks are used. In certain embodiments, the predefined threshold is based on a number of possible preprocessing tasks done in a predefined period. For example, a five-minute delay from scan to reading room may be set. The predefined threshold may be set to limit the preprocessing tasks to those that may fit within the five-minute period so as not to generate wait times for the user in the reading room. The predefined threshold may be set to only include those preprocessing tasks that are better than average (e.g. better than 50%).

In certain embodiments, the plurality of preprocessing tasks that were implemented are saved in the database 120 for future use. For a subsequent scan with a similar scan protocol, the same preprocessing tasks may be implemented. As new usage data is collected, the scores and ranking of the preprocessing tasks may change.

For a new scan protocol, the server may use usage data for similar scans. For example, a new scan protocol using a medical device A for a body region B may query usage data for similar medical devices, modalities, or scanned body regions. For a new scan protocol, a notification may be sent to an administrator. The notification may further be sent to a technician who ordered or operated the medical imaging device. A notification may be sent to a vendor requesting any information for best practices.

For scan data that does not have a recognizable scan protocol, attributes from the image data may be used to generate a placeholder scan protocol. The placeholder scan protocol may be treated as a new scan protocol detailed above. The usage data for similar medical devices, modalities, or scanned regions may be used to select preprocessing tasks.

Figure 4:
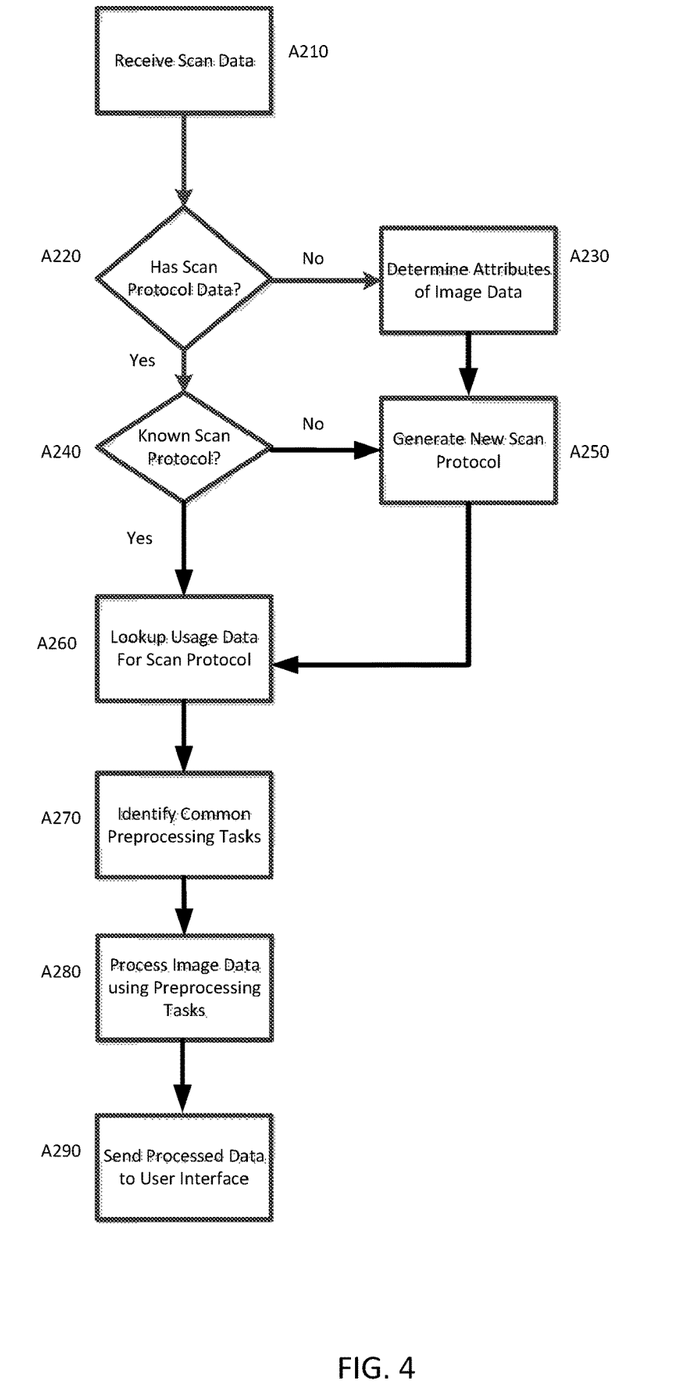
FIG. 4 depicts an example workflow for preprocessing image data based on scan protocols.

FIG. 4 illustrates an example workflow for preprocessing image data based on scan protocols. In one embodiment, the acts are performed by the preprocessing server 125, the preprocessing engine 140, or one or more of the imaging devices 107. In an embodiment, the workflow is performed using cloud computing. Additional, different, or fewer acts may be provided. The acts are performed in the order shown or other orders. The acts may also be repeated.

At act A210, scan data is received for a scan. Scan data may be generated by a medical imaging device 107. The scan data may include image data and attributes or parameters related to the scan. The scan data may include metadata relating to the scan.

At act A220, the scan data is analyzed for a scan protocol. A scan protocol may include a predefined set of parameters. Similar types of scans may have similar or the same scan protocol. The scan protocol may be indicated by the modality and region of the patient that was scanned. The scan protocol may be indicated by other parameters.

If the scan data does not have a scan protocol, the workflow proceeds to A230. If the scan data has a protocol, the workflow proceeds to A240. At act A230, if the scan data does not have a scan protocol, the scan data is analyzed for attributes. The attributes may include, for example, the modality or region of the patient. The attributes may include data related to the type of equipment that originally acquired the scan data. The attributes may include data related to the manufacturer. The attributes may include data related to the manufacturer's model name. The attributes may include a description of the study or series of images. The attributes may include further data such as an identifier for the acquisition protocol, the target region, the acquisition type, the procedure context, the acquisition parameters (e.g. exposure time, scanning length), the dose etc. Once the attributes have been identified, the workflow proceeds to act A250.

At act A250, a new scan protocol is generated in the preprocessing database 120. A new scan protocol may be generated based on the attributes or parameters of the scan. The new scan protocol may be assigned a unique identifier. A notification of the new scan protocol may be transmitted to the medical imaging device 107 or an administrator. The new scan protocol may be stored in the preprocessing database 120.

At act A240, if the scan data does include an identifiable scan protocol, the scan protocol is queried in a preprocessing database 120. If the scan protocol is not found in the preprocessing database 120, the workflow proceeds to act A250. If the scan protocol is found in the preprocessing database 120, the workflow proceeds to act A260.

At act A260, usage data (e.g. historical use data relating to prior preprocessing of image for similar scan protocols) is identified in the preprocessing database 120. The usage data may include data relating to the use of preprocessed data by one or more users. A user may or may not use a preprocessed image to make an evaluation. The user's action may be record and designed usage data for the preprocessed image. The usage data for the preprocessed image may be imputed to the preprocessing tasks performed for the image.

At act A270, common preprocessing tasks are identified for the scan protocol. From the usage data of act A260, common preprocessing tasks may be identified. Any statistical analysis of prior usage of tasks for a given scan protocol may be used. The preprocessing tasks that were used more often than a predefined threshold or average may be identified as common. Other criteria may be used, such as the efficiency of the preprocessing tasks, the success rate in generating a useful image, user rating, vendor ratings, among others.

At act A280, the image data is processed using the common preprocessing tasks. The image data may be processed using tasks in the order of the most common to least common. The most successful tasks may be processed first. Only preprocessing tasks above a predefined threshold may be used.

At act A290, the preprocessed data is transmitted to a user interface for evaluation. The evaluation of the preprocessed data may generate usage data that is then stored with the scan protocol and the preprocessing tasks in the preprocessing database 120.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking may be advantageous. Moreover, the separation of various system components in the embodiments described above should not be understood as requiring such separation in all embodiments One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing detailed description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the detailed description provided herein, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

We claim:

1. A system for preprocessing medical scan data acquired from a medical imaging device, the system comprising:
    the medical imaging device configured to acquire medical scan data using a scan protocol;
    a processor configured to collect usage data for a plurality of preprocessing tasks performed on medical scan data acquired using the medical imaging device with different scan protocols, the usage data including how often a preprocessing task leads to a useful result for each scan protocol, a number of resources consumed by the preprocessing task, and user ratings collected at a beginning or an end of an evaluation of preprocessed medical scan data, the processor further configured to calculate a score for each of the plurality of preprocessing tasks as a function of the usage data;
    a database configured to store the plurality of preprocessing tasks and the scores for each of the plurality of preprocessing tasks;
    the processor configured, after receiving medical imaging data from the medical imaging device, to select one or more preprocessing tasks of the plurality of preprocessing tasks as a function of the scan protocol and the score for each of the plurality of preprocessing tasks, wherein the processor is further configured to execute the one or more preprocessing tasks on the medical scan data prior to transmitting the data to a reading workstation; and
    the reading workstation configured to display or present image data to a technician or end user, the reading workstation configured to receive the preprocessed medical scan data, the reading workstation further configured to store the usage data for the preprocessed medical scan data in the database to be used in updating the scores for the plurality of preprocessing tasks.

2. The system of claim 1, wherein the medical scan data and the scan protocol are formatted with DICOM.

3. The system of claim 1, wherein the scan protocol includes data relating to a modality and body region of a scan.

4. The system of claim 1, wherein the processor is further configured to rank the one or more preprocessing tasks based on the usage data, wherein the one or more preprocessing tasks are executed based on the ranking.

5. The system of claim 1, wherein the one or more preprocessing tasks comprise preprocessing tasks that have been previously used for previous medical scan data with the same scan protocol.

6. The system of claim 1, wherein the scan protocol is included in a MPPS message.

7. The system of claim 1, the scan protocol comprises data relating to a body region of the scan.

8. A method comprising:
    collecting usage data for a plurality of preprocessing tasks performed on medical scan data collected using a scan protocol over a period of time, the usage data including how often a preprocessing task leads to a useful result for each scan protocol and user ratings collected at a beginning or an end of an evaluation of preprocessed medical scan data;
    calculate a score for each of the plurality of preprocessing tasks as a function of the usage data;
    ranking the plurality of preprocessing tasks for the scan protocol based on the scores;
    receiving medical scan data of a patient including scan protocol data for a scan by a medical imaging device;
    querying a database for the plurality of preprocessing tasks and respective ranks related to the scan protocol data;
    and
    performing the plurality of preprocessing tasks on the medical scan data in the ranked order.

9. The method of claim 8, further comprising:
    transmitting the preprocessed medical scan data to a user interface.

10. The method of claim 8, further comprising:
    updating the usage data with one or more uses from a user interface.

11. The method of claim 8, wherein performing comprises:
    identifying one or more preprocessing tasks of the plurality of preprocessing tasks that rank above a predefined threshold; and performing the one or more preprocessing tasks that rank above the predefined threshold and not performing the preprocessing tasks that rank below the predefined threshold.

12. The method of claim 11, wherein the predefined threshold is defined by an amount of available processing resources.

13. The method of claim 11, wherein the predefined threshold is 50% or more.

14. An apparatus comprising:
at least one processor; and
at least one memory including computer program code for one or more programs; the at least one memory and the computer program code configured to, with the at least one processor, cause the apparatus to at least perform:
collect usage data for a plurality of preprocessing tasks performed on medical scan data acquired using a medical imaging device using different scan protocols;
identify a success rate for each of the plurality of preprocessing tasks as a function of how often a preprocessing task leads to a useful result for each scan protocol;
receive user ratings collected at an end of an evaluation of preprocessed medical scan data for each scan protocol;
score each of the plurality of preprocessing tasks as a function of the success rates and the user ratings;
receive, by the processor, medical scan data from a scan including image data of a patient and a scan protocol;
process, automatically by the processor, the image data using the scored preprocessing tasks, wherein the higher scored preprocessing tasks of the plurality of preprocessing tasks are processed first; and
transmit, by the processor, the processed image data to a workstation.

15. The apparatus of claim 14, wherein the scan protocol comprises a MPPS message.

16. The apparatus of claim 14, wherein the scan protocol comprises data relating to a body region of the scan.

17. The apparatus of claim 14, wherein the scan protocol comprises data relating to a user.

18. The apparatus of claim 14, wherein the score is calculated as a function of historical usage data.

* * * * *